United States Patent [19]
Hommeltoft et al.

[11] Patent Number: 5,648,522
[45] Date of Patent: Jul. 15, 1997

[54] PROCESS FOR THE SYNTHESIS OF FLUORINATED SULPHONIC ACIDS

[75] Inventors: Sven Ivar Hommeltoft, Hillerød; Ole Ekelund, Lyngby; John Zavilla, Vedbæk, all of Denmark

[73] Assignee: Haldor Topsøe A/S, Lyngby, Denmark

[21] Appl. No.: 596,568

[22] Filed: Feb. 5, 1996

[30] Foreign Application Priority Data

Feb. 14, 1995 [DK] Denmark ................................ 0168/95

[51] Int. Cl.$^6$ ................................................. C07C 309/06
[52] U.S. Cl. ................................................. 562/83
[58] Field of Search ................................................. 562/83

[56] References Cited

U.S. PATENT DOCUMENTS

| | | |
|---|---|---|
| 1,189,562 | 7/1916 | Groehn et al. |
| 2,732,398 | 1/1956 | Brice et al. |
| 2,877,267 | 3/1959 | Van Dyke Tiers et al. |
| 3,542,864 | 11/1970 | Koshar. |
| 3,919,295 | 11/1975 | Wechsberg et al. |

*Primary Examiner*—Nicky Chan
*Attorney, Agent, or Firm*—Ostrolenk, Faber, Gerb & Soffen, LLP

[57] ABSTRACT

Process for the preparation of a fluorinated sulphonic acid compound by hydrolysis of a corresponding fluorinated sulphonyl fluoride, wherein the hydrolysis is carried out in the presence of a tertiary amine, comprising steps of recovering a mixture of a salt of hydrolysed fluorinated sulphonyl fluoride with the tertiary amine and an ammonium fluoride salt of the tertiary amine;

reacting the salt mixture with a sulphonyl compound of the general formula R—SO$_2$X, wherein R=an alkyl group, Cl, F;

and

X=Br, Cl thereby exchanging fluoride of the ammonium fluoride salt in the mixture with the X atom of the sulphonyl compound and converting the sulphonyl compound to a sulphonyl fluoride; and distilling off the sulphonyl fluoride from the reacted salt mixture.

4 Claims, No Drawings

PROCESS FOR THE SYNTHESIS OF FLUORINATED SULPHONIC ACIDS

The present invention is directed to the preparation of fluorinated sulphonic acid compounds. In particular, the invention concerns certain improvements in the recovery of salts of fluorinated sulphonyl acids obtained during hydrolysis of fluorinated sulphonyl fluorides being an important step in the preparation of fluorinated sulphonic acids.

The ordinary synthesis route of fluorinated sulphonic acids involves hydrolysis of fluorinated sulphonyl fluorides, whereby a mixture of salts comprising a fluoride salt and a salt of the fluorinated sulphonic acid is obtained.

Fluorinated sulphonyl fluorides may be prepared in several ways, like electrochemical fluorination of corresponding alkane sulphonyl halides or cyclic sulphones in anhydrous HF (U.S. Pat. No. 2,732,398, DE Offenlegungsschrift No. 2,725,211, DE Offenlegungsschrift No. 1,912,738, DE Offenlegungsschrift No. 4,208,364, DE Offenlegungsschrift No. 4,218,562 and DE Offenlegungsschrift No. 4,226,758). Furthermore, it is known to prepare perfluorinated sulphonyl fluorides by addition of sulphuryl difluoride or sulphuryl chloride fluoride to fluoro-olefins (U.S. Pat. Nos. 1,189,562, 2,877,267, DE Auslegenschrift No. 1,668,584, FR Patent No. 1,573,537, U.S. Pat. No. 3,542,864).

Hydrolysis of sulphonyl fluorides is in the known preparation processes performed by contacting the fluorides with an aqueous alkaline solution, such as solutions of KOH, NaOH or $NH_4OH$. The product from the hydrolysis step is an aqueous solution of salts, from which a salt of the fluorinated sulphonic acid is recovered as a solid.

Further synthesis steps involve distillation of the anhydrous salt of the fluorinated sulphonic acid by use of a strong acid such as concentrated sulphuric acid to anhydrous fluorinated sulphonic acid. Prior to distillation, fluoride ions, which are converted to HF with sulphuric acid, have to be removed because of the corrosive nature of HF. Removal of fluoride ions is usually accomplished by precipitation of fluoride salts with low solubility, such as barium fluoride, or by extraction of fluorinated sulphonic acid salt from a mixture of salts from the hydrolysis step. In both cases, the known preparation processes involve handling of solids and drying of salts, which complicates the processes.

It has now been found that preparation of fluorinated sulphonic acids may be improved, when carrying out hydrolysis of corresponding sulphonic fluorides in a solution with a tertiary amine solvent and reacting fluoride salts formed during the hydrolysis with a sulphonyl chloride or bromide compound to corresponding salts, from which the fluorinated sulphonic acid is recovered.

In accordance with the above finding, this invention provides a process for the preparation of a fluorinated sulphonic acid compound by hydrolysis of a corresponding fluorinated sulphonyl fluoride in presence of a tertiary amine, comprising further steps of recovering a mixture of a salt of hydrolysed fluorinated sulphonyl fluoride with the tertiary amine and an ammonium fluoride salt of the tertiary amine;

reacting the salt mixture with a sulphonyl compound of the general formula R—$SO_2$X, wherein R=an alkyl group, Cl, F;

and

X=Br, Cl thereby exchanging fluoride of the ammonium fluoride salt in the mixture with the X atom of the sulphonyl compound and converting the sulphonyl compound to a sulphonyl fluoride and distilling off the sulphonyl fluoride from the reacted salt mixture.

The sulphonic acid compound may finally be recovered by treating the remanence from the distillation step with a proton donating acid and distilling off the fluorinated sulphonic acid compound.

Alternatively, the salt mixture is alkalized with an alkaline solution and tertiary amine being separated prior to protonization of the salt mixture.

The reaction of the salt mixture with the sulphonyl compound may proceed under anhydrous conditions and produces then a dry salt mixture containing salts of the fluorinated sulphonic acid and tertiary ammonium chloride or bromide salts. This mixture can be distilled directly from sulphuric acid in glass apparatus to a fraction with hydrogen bromide or chloride and a fraction of the anhydrous perfluorinated sulphonic acid.

Suitable amines for use as solvent in the above process are the tertiary amines, which do not form amides with the hydrolysed fluoride acid compounds. Preferred are tertiary amines, which form low melting salts with the hydrolysis product. Presently, most preferred amines are trialkyl amines with identical or different $C_1$–$C_{20}$ alkyl groups.

Preferred sulphonyl compounds for the fluoride exchange will be those which after the fluoride exchange can be used as starting materials in an electrochemical fluorination reaction for the preparation of the fluorinated sulphonyl fluorides starting materials in the above process.

EXAMPLE 1

To 9.7 g of a 1:1 mixture of pyridinium perfluoropropane-1-sulphonate ($CF_3CF_2CF_2SO_3HNC_5H_5$) and pyridinium hydrofluoride ($FHNC_5H_5$) (prepared by the reaction of perfluoropropane 1-sulphonyl fluoride with less than 1 equivalent of water in the presence of an excess pyridine) were added 26 ml (336 mmole, 10 equivalents relative to fluoride) methane sulphonyl chloride and the mixture was heated to 75–80° C. for 30 minutes. Excess methane sulphonyl chloride was then removed together with produced methane sulphonyl fluoride by evaporation under reduced pressure (0.75 psi) leaving 11.1 g of a crystalline mixture of pyridinium perfluoropropane-1-sulphonate ($CF_3CF_2CF_2SO_3HNC_5H_5$) and pyridinium hydrochloride ($ClHNC_5H_5$) with a fluoride content of 0.1%.

EXAMPLE 2

To 6.8 g of a 1:1 mixture of triethylammonium perfluoropropane-1-sulphonate ($CF_3CF_2CF_2SO_3HNEt_3$) and triethylammonium hydrofluoride ($FHNEt_3$) (prepared by the reaction of perfluoropropane 1-sulphonyl fluoride with less than 1 equivalent of water in the presence of an excess triethyl amine) were added 7.5 ml (97 mmole, 3 equivalents relative to fluoride) methane sulphonyl chloride and the mixture was heated to 75–80° C. for 90 minutes. Additional 40 ml methane sulphonyl chloride were added. Excess methane sulphonyl chloride was removed together with produced methane sulphonyl fluoride by slow evaporation over 1 hr at reduced pressure (0.75 psi) leaving 12.4 g of a viscous liquid salt mixture triethylammonium perfluoropropane-1-sulphonate ($CF_3CF_2CF_2SO_3HNEt_3$) and triethylammonium hydrochloride ($ClHNEt_3$) with a fluoride content of 410 ppm.

EXAMPLE 3

110 ml (1.42 moles) methane sulphonyl chloride ($CH_3SO_2Cl$) were placed in a 250 ml flask with a 30 cm packed column. On the top of the column was arranged a 2-way adapter with a pressure-equilibrated addition funnel and a Vigreaux column. The top of the Vigreaux column was connected to a Liebig condenser and a collecting flask for the collection of distilled material. The collecting flask was under vacuum (0.75 psi). The methane sulphonyl chloride was heated to reflux. 24.7 g of an anhydrous 1:1 mixture of triethylammonium perfluoropropane-1-sulphonate ($CF_3CF_2CF_2SO_3HNEt_3$) and triethylammonium hydrofluoride ($FHNEt_3$) (prepared by the reaction of perfluoropropane 1-sulphonyl fluoride with less than 1 equivalent of water in the presence of an excess triethyl amine) were added from the addition funnel to the top of the packed column over 90 minutes. Methane sulphonyl chloride reflux was maintained throughout the addition. At the end of the addition, excess methane sulphonyl chloride together with produced methane sulphonyl fluoride were distilled over in the collecting flask leaving 27.5 g of a 1:1 mixture of triethylammonium perfluoropropane-1-sulphonate ($CF_3CF_2CF_2SO_3HNEt_3$) and triethylammonium hydrochloride ($ClHNEt_3$) with a fluoride content of 60 ppm.

EXAMPLE 4

100 ml (1.29 moles) methane sulphonyl chloride ($CH_3SO_2Cl$) were added to a 250 ml flask with a 30 cm packed column. On the top of the column was a arranged 2-way adapter with a pressure-equilibrated addition funnel and a Vigreaux column. The top of the Vigreaux column was connected to a Liebig condenser and a collecting flask for the collection of distilled material. The collecting flask was held under to vacuum (0.75 psi), and the methane sulphonyl chloride heated to reflux. 33.1 g of an anhydrous 1:1 mixture of tributylammonium perfluoro-octane-l-sulphonate ($CF_3(CF_2)_7SO_3HNBu_3$) and trietylammonium hydrofluoride ($FHNBu_3$) (prepared by the reaction of perfluoro-octane 1-sulphonyl fluoride with less than 1 equivalent of water in the presence of an excess tributyl amine) were added from the addition funnel to the top of the packed column over 100 minutes. A method of methane sulphonyl chloride and a slow distillation were maintained throughout the addition.

At the end of the addition excess methane sulphonyl chloride and methane sulphonyl fluoride were distilled over in the collecting flask leaving 34.2 g of a 1:1 mixture of tributylammonium perfluoro-octane-1-sulphonate ($CF_3(CF_2)_7SO_3HNBu_3$) and tributylammonium hydrochloride ($ClHNBu_3$) as a highly viscous liquid with a fluoride content of 93 ppm.

We claim:

1. Process for the preparation of a fluorinated sulphonic acid compound by hydrolysis of a corresponding fluorinated sulphonyl fluoride in the presence of a tertiary amine, comprising steps of (a) recovering a mixture of a salt of hydrolysed fluorinated sulphonyl fluoride with the tertiary amine and an ammonium fluoride salt of the tertiary amine;

(b) reacting the salt mixture with a sulphonyl compound of the general formula R—$SO_2X$, wherein R=an alkyl group, Cl, F;

and

X=Br, Cl and exchanging fluoride of the ammonium fluoride salt in the mixture with the X atom of the sulphonyl compound and converting the sulphonyl compound to a sulphonyl fluoride;

(c) distilling off the sulphonyl fluoride from the reacted salt mixture of step (b).

2. The process of claim 1, wherein the tertiary amine comprises trialkyl amines of the general formula $R^1R^2R^3N$, $R^1$, $R^2$, $R^3$ are identical or different $C_1$–$C_{20}$ alkyl groups.

3. The process of claim 1, wherein the tertiary amine comprises aromatic tertiary amines.

4. The process of claim 1, wherein the sulphonyl compound after fluoride exchange corresponds to the fluorinated sulphonyl fluoride.

* * * * *